US010137061B2

(12) United States Patent
Rusin et al.

(10) Patent No.: US 10,137,061 B2
(45) Date of Patent: Nov. 27, 2018

(54) DENTAL FILLERS AND COMPOSITIONS INCLUDING PHOSPHATE SALTS

(75) Inventors: Richard P. Rusin, Woodbury, MN (US); Sumita B. Mitra, West St. Paul, MN (US); Kevin M. Cummings, Little Canada, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 2011 days.

(21) Appl. No.: 11/719,469

(22) PCT Filed: Nov. 7, 2005

(86) PCT No.: PCT/US2005/040339
§ 371 (c)(1),
(2), (4) Date: Apr. 15, 2009

(87) PCT Pub. No.: WO2006/055327
PCT Pub. Date: May 26, 2006

(65) Prior Publication Data
US 2009/0208909 A1  Aug. 20, 2009

Related U.S. Application Data

(63) Continuation of application No. 10/989,780, filed on Nov. 16, 2004, now abandoned.

(51) Int. Cl.
A61K 6/08 (2006.01)
A61K 6/00 (2006.01)
A61K 6/083 (2006.01)
A61K 6/087 (2006.01)

(52) U.S. Cl.
CPC .......... *A61K 6/0017* (2013.01); *A61K 6/0023* (2013.01); *A61K 6/0088* (2013.01); *A61K 6/0091* (2013.01); *A61K 6/083* (2013.01); *A61K 6/087* (2013.01)

(58) Field of Classification Search
CPC .................................................. A61K 6/0017
USPC ........................................................ 523/116
See application file for complete search history.

(56) References Cited

U.S. PATENT DOCUMENTS

| | | |
|---|---|---|
| 2,323,550 A | 7/1943 | Lukens |
| 3,018,262 A | 1/1962 | Schroeder |
| 3,786,116 A | 1/1974 | Milkovich et al. |
| 3,804,794 A | 4/1974 | Schmitt et al. |
| 3,842,059 A | 10/1974 | Milkovich et al. |
| 3,926,870 A | 12/1975 | Keegan et al. |
| 4,141,864 A * | 2/1979 | Rijke et al. ........... 523/114 |
| 4,198,394 A | 4/1980 | Faunce |
| 4,259,075 A | 3/1981 | Yamauchi et al. |
| 4,298,738 A | 11/1981 | Lechtken et al. |
| 4,324,744 A | 4/1982 | Lechtken et al. |
| 4,356,296 A | 10/1982 | Griffith et al. |
| 4,385,109 A | 5/1983 | Lechtken et al. |
| 4,397,837 A | 8/1983 | Raaf |
| 4,499,251 A | 2/1985 | Omura et al. |
| 4,503,169 A | 3/1985 | Randklev |
| 4,518,430 A | 5/1985 | Brown et al. |
| 4,537,940 A | 8/1985 | Omura et al. |
| 4,539,382 A | 9/1985 | Omura et al. |
| 4,612,053 A | 9/1986 | Brown et al. |
| 4,642,126 A | 2/1987 | Zador et al. |
| 4,648,843 A | 3/1987 | Mitra |
| 4,652,274 A | 3/1987 | Boettcher et al. |
| 4,684,673 A | 8/1987 | Adachi |
| 4,695,251 A | 9/1987 | Randklev |
| 4,698,318 A | 10/1987 | Vogel et al. |
| 4,710,523 A | 12/1987 | Lechtken et al. |
| 4,737,593 A | 4/1988 | Ellrich et al. |
| 4,871,786 A | 10/1989 | Aasen et al. |
| 4,872,936 A | 10/1989 | Engelbrecht |
| 4,880,660 A | 11/1989 | Aasen et al. |
| 5,015,628 A | 5/1991 | Reynolds |
| 5,037,639 A | 8/1991 | Tung |
| 5,055,497 A | 10/1991 | Okada et al. |
| 5,074,916 A | 12/1991 | Hench et al. |
| 5,076,844 A | 12/1991 | Fock et al. |
| 5,130,347 A | 7/1992 | Mitra |
| 5,135,396 A | 8/1992 | Kuboki |
| 5,154,762 A | 10/1992 | Mitra et al. |
| 5,162,267 A | 11/1992 | Smyth |
| 5,192,815 A | 3/1993 | Okada et al. |

(Continued)

FOREIGN PATENT DOCUMENTS

| | | |
|---|---|---|
| CA | 2098039 | 12/1994 |
| DE | 10242075 | 3/2004 |

(Continued)

OTHER PUBLICATIONS

Ana et al. "Effects of added bioactive glass on the setting and mechanical properties of resin-modified glass ionomer cement" *Biomaterials*, Elsevier Science Publishers BV., Barking, GB, vol. 24, No. 18, Aug. 2003, pp. 3061-3067, ISSN: 0142-9612.
ANSI/ADA Spec. No. 27 "Resin-Based Filling Materials," pp. 1-27 (1993).
ASTM D2805-959, ."Standard Test Method for Hiding Power of Paints by Reflectometry," 1995, pp. 115-119.
Cao et al. "Bioactive Materials" *Ceramics International*, Elsevier, Amsterdam, NL, 1996; 22(6):493-507.
*CRC Handbook of Chemistry and Physics*, 51st Edition, The Chemical Rubber Co., Cleveland, OH, Title page, copyright page, and p. B-77 (1970).
Data Sheet: Comparison of RECALDENT (PP-ACP) Technology, GC America Inc., Dec. 2006, 1 pg.
Hench et al., "Bioactive Glasses," *An Introduction to Bioceramics*, L.L. Hench & J. Wilson, Eds., World Scientific Publishing (1993), Chapter 3, pp. 41-61.

(Continued)

*Primary Examiner* — Michael Pepitone

(57) ABSTRACT

The present application provides dental fillers, and methods of making and using dental fillers that include a treated surface that includes a phosphate salt. Dental compositions including such dental fillers can be useful for delivering ions to the oral environment. Dental compositions, and methods of using dental compositions that include a phosphate salt and a hardenable resin or a water-dispersible, polymeric film former are also provided.

17 Claims, No Drawings

(56) References Cited

U.S. PATENT DOCUMENTS

| | | |
|---|---|---|
| 5,296,026 A | 3/1994 | Monroe et al. |
| 5,332,429 A | 7/1994 | Mitra et al. |
| 5,340,776 A | 8/1994 | Paschke et al. |
| 5,468,477 A | 11/1995 | Kumar et al. |
| 5,501,727 A | 3/1996 | Wang et al. |
| 5,508,342 A | 4/1996 | Antonucci et al. |
| 5,525,648 A | 6/1996 | Aasen et al. |
| 5,530,038 A | 6/1996 | Yamamoto et al. |
| 5,545,676 A | 8/1996 | Palazzotto et al. |
| 5,571,502 A | 11/1996 | Winston et al. |
| 5,603,922 A | 2/1997 | Winston et al. |
| 5,607,663 A | 3/1997 | Rozzi et al. |
| 5,614,175 A | 3/1997 | Winston et al. |
| 5,641,347 A | 6/1997 | Grabowski et al. |
| 5,662,887 A | 9/1997 | Rozzi et al. |
| 5,693,313 A | 12/1997 | Shiraishi et al. |
| 5,725,882 A | 3/1998 | Kumar et al. |
| 5,735,942 A | 4/1998 | Litkowski et al. |
| 5,762,950 A | 6/1998 | Yli-Urpo et al. |
| 5,817,296 A | 10/1998 | Winston |
| 5,833,957 A | 11/1998 | Winston et al. |
| 5,858,333 A | 1/1999 | Winston |
| 5,866,102 A | 2/1999 | Winston |
| 5,866,630 A | 2/1999 | Mitra et al. |
| 5,876,208 A | 3/1999 | Mitra et al. |
| 5,883,153 A | 3/1999 | Roberts et al. |
| 5,888,491 A | 3/1999 | Mitra et al. |
| 5,891,233 A | 4/1999 | Salonen et al. |
| 5,891,448 A | 4/1999 | Chow et al. |
| 5,895,641 A | 4/1999 | Usen |
| 5,910,273 A | 6/1999 | Thiel et al. |
| 5,922,786 A | 7/1999 | Mitra et al. |
| 5,958,915 A | 9/1999 | Abe et al. |
| 5,980,697 A | 11/1999 | Kolb et al. |
| 5,981,475 A | 11/1999 | Reynolds |
| 5,993,786 A | 11/1999 | Chow |
| 6,030,606 A | 2/2000 | Holmes |
| 6,036,494 A | 3/2000 | Cohen |
| 6,036,762 A | 3/2000 | Sambasivan |
| 6,036,944 A | 3/2000 | Winston et al. |
| 6,056,930 A | 5/2000 | Tung |
| 6,063,832 A | 5/2000 | Yuhda et al. |
| 6,086,374 A | 7/2000 | Litkowski et al. |
| 6,136,737 A | 10/2000 | Todo et al. |
| 6,136,885 A | 10/2000 | Rusin et al. |
| 6,159,449 A | 12/2000 | Winston |
| 6,180,688 B1 | 1/2001 | Rheinberger et al. |
| 6,244,871 B1 | 6/2001 | Litkowski et al. |
| 6,251,963 B1 | 6/2001 | Köhler et al. |
| 6,270,562 B1 | 8/2001 | Jia |
| 6,297,181 B1 | 10/2001 | Kunert et al. |
| 6,306,926 B1 | 10/2001 | Bretscher et al. |
| 6,312,668 B2 | 11/2001 | Mitra et al. |
| 6,312,688 B1 | 11/2001 | Poustka |
| 6,338,751 B1 | 1/2002 | Litkowski et al. |
| 6,353,039 B1 | 3/2002 | Rheinberger et al. |
| 6,355,271 B1 | 3/2002 | Bell |
| 6,355,704 B1 | 3/2002 | Nakatsuka et al. |
| 6,372,198 B1 | 4/2002 | Abbate |
| 6,387,981 B1 | 5/2002 | Zhang et al. |
| 6,398,859 B1 | 6/2002 | Dickens et al. |
| 6,413,538 B1 | 7/2002 | Garcia et al. |
| 6,426,114 B1 | 7/2002 | Troczynski et al. |
| 6,437,019 B1 | 8/2002 | Rusin et al. |
| 6,451,290 B2 | 9/2002 | Winston et al. |
| 6,458,868 B1 | 10/2002 | Okada et al. |
| 6,461,632 B1 * | 10/2002 | Gogolewski ............ 424/426 |
| 6,521,264 B1 | 2/2003 | Lacout et al. |
| 6,572,693 B1 | 6/2003 | Wu et al. |
| 6,596,061 B1 | 7/2003 | Rentschler |
| 6,613,812 B2 | 9/2003 | Bui et al. |
| 6,632,412 B2 | 10/2003 | Peltola et al. |
| 6,649,669 B2 | 11/2003 | Dickens |
| 6,652,875 B1 | 11/2003 | Bannister |
| 6,709,744 B1 | 3/2004 | Day et al. |
| 6,730,156 B1 | 5/2004 | Windisch et al. |
| 6,733,818 B2 | 5/2004 | Luo et al. |
| 6,750,268 B2 | 6/2004 | Hino |
| 6,765,036 B2 | 7/2004 | Dede et al. |
| 6,770,265 B2 | 8/2004 | Ishihara et al. |
| 6,770,325 B2 | 8/2004 | Troczynski et al. |
| 6,780,844 B1 | 8/2004 | Reynolds |
| 6,790,877 B2 | 9/2004 | Nakatsuka et al. |
| 6,793,725 B2 | 9/2004 | Chow |
| 6,818,682 B2 | 11/2004 | Falsafi et al. |
| 6,923,989 B2 | 8/2005 | Lacout et al. |
| 6,960,079 B2 | 11/2005 | Brennan et al. |
| 6,982,288 B2 | 1/2006 | Mitra et al. |
| 7,090,720 B2 | 8/2006 | Kessler et al. |
| 7,090,721 B2 | 8/2006 | Craig et al. |
| 7,156,911 B2 | 1/2007 | Kangas et al. |
| 7,173,074 B2 | 2/2007 | Mitra et al. |
| 7,255,562 B2 | 8/2007 | Rusin et al. |
| 2003/0082232 A1 | 5/2003 | Lee et al. |
| 2003/0157357 A1 | 8/2003 | Rusin et al. |
| 2003/0158302 A1 | 8/2003 | Chaput et al. |
| 2003/0167967 A1 | 9/2003 | Narhi et al. |
| 2003/0181541 A1 | 9/2003 | Wu et al. |
| 2004/0052860 A1 | 3/2004 | Reid et al. |
| 2004/0138759 A1 * | 7/2004 | Muller et al. .............. 623/23.62 |
| 2004/0185013 A1 | 9/2004 | Burgio et al. |
| 2004/0206932 A1 | 10/2004 | Abuelyaman |
| 2004/0241238 A1 | 12/2004 | Sepulveda et al. |
| 2005/0020720 A1 | 1/2005 | Dickens |
| 2005/0175965 A1 | 8/2005 | Craig et al. |
| 2005/0175966 A1 | 8/2005 | Falsafi et al. |
| 2005/0176844 A1 | 8/2005 | Aasen et al. |
| 2005/0201987 A1 | 9/2005 | Pirhonen et al. |
| 2005/0256223 A1 | 11/2005 | Kolb et al. |
| 2007/0178220 A1 | 8/2007 | Karlinsey |
| 2008/0187500 A1 | 8/2008 | Karlinsey |

FOREIGN PATENT DOCUMENTS

| | | |
|---|---|---|
| EP | 0 173 567 A2 | 3/1986 |
| EP | 0 201 031 A2 | 11/1986 |
| EP | 0 201 778 A1 | 11/1986 |
| EP | 0 201 778 B1 | 12/1988 |
| EP | 0 201 031 B1 | 8/1989 |
| EP | 0 344 832 A1 | 12/1989 |
| EP | 0 373 384 A1 | 6/1990 |
| EP | 0 344 832 B1 | 10/1992 |
| EP | 0 373 384 B1 | 10/1992 |
| EP | 0 634 373 A1 | 1/1995 |
| EP | 0 712 622 A1 | 5/1996 |
| EP | 0 712 622 B1 | 9/1999 |
| EP | 1 051 961 A1 | 11/2000 |
| EP | 1 285 646 A1 | 2/2003 |
| EP | 1 051 961 B1 | 2/2006 |
| GB | 1 434 081 | 4/1976 |
| GB | 1532318 A * | 11/1978 |
| GB | 1 560 992 | 2/1980 |
| JP | 4-198112 | 7/1992 |
| JP | 4-329960 | 11/1992 |
| JP | 06-199622 | 7/1994 |
| JP | 6-321515 | 11/1994 |
| JP | 9703843 | 4/1998 |
| JP | 10167942 | 6/1998 |
| RU | 1 792 695 | 2/1993 |
| WO | WO 87/07615 | 12/1987 |
| WO | WO 93/12760 A1 | 7/1993 |
| WO | WO 95/22956 A1 | 8/1995 |
| WO | WO 97/36943 | 10/1997 |
| WO | WO 98/17236 | 4/1998 |
| WO | WO 99/07326 A2 | 2/1999 |
| WO | WO 99/07326 A3 | 2/1999 |
| WO | WO 99/34772 A1 | 7/1999 |
| WO | WO 00/06108 A1 | 2/2000 |
| WO | WO 00/38619 A2 | 7/2000 |
| WO | WO 00/40206 A1 | 7/2000 |
| WO | WO 00/42092 A1 | 7/2000 |
| WO | WO 01/07444 A1 | 2/2001 |
| WO | WO 01/30305 A1 | 5/2001 |
| WO | WO 01/30306 A1 | 5/2001 |

(56) References Cited

FOREIGN PATENT DOCUMENTS

| WO | WO 01/30307 A1 | 5/2001 |
|---|---|---|
| WO | WO 01/41822 A1 | 6/2001 |
| WO | WO 01/92271 A1 | 12/2001 |
| WO | WO 02/49578 | 6/2002 |
| WO | WO 02/072038 A1 | 9/2002 |
| WO | WO 02/085313 A1 | 10/2002 |
| WO | WO 02/094204 A1 | 11/2002 |
| WO | WO 03/052164 A2 | 6/2003 |
| WO | WO 03/063804 A1 | 8/2003 |
| WO | WO 03/074009 A1 | 9/2003 |
| WO | WO 03/095085 | 11/2003 |
| WO | WO 04/000252 A1 | 12/2003 |
| WO | WO 04/035029 A1 | 4/2004 |
| WO | WO 04/035077 A1 | 4/2004 |
| WO | WO 04/060327 A1 | 7/2004 |
| WO | WO 05/018581 A2 | 3/2005 |
| WO | WO 05/018581 A3 | 3/2005 |
| WO | WO 2005-074453 | 8/2005 |
| WO | WO 06/020760 A1 | 2/2006 |
| WO | WO 06/055317 A1 | 5/2006 |
| WO | WO 06/055328 A1 | 5/2006 |
| WO | WO 06/055329 A2 | 5/2006 |
| WO | WO 06/055329 A3 | 5/2006 |
| WO | WO 2008/147997 | 12/2008 |

OTHER PUBLICATIONS

Höland et al., "Machineable and Phosphate Glass-Ceramics," *An Introduction to Bioceramics*, L.L. Hench & J. Wilson, Eds., World Scientific Publishing (1993), Chapter 8, pp. 125-136.
IUPAC Nomenclature of Inorganic Chemistry, Recommendations 1990.
Kawakami et al., "Silicone Macromers for Graft Polymer Synthesis," *Polymer J.*, 1982; 14:913-917.
Kawakami et al., "Synthesis and Copolymerization of Polysiloxane Macromers," ACS Polymer Preprints, 1984; 25(1):245-246.
Kawakami et al., "Synthesis of Silicone Graft Polymers and a Study of Their Surface Active Properties," *Makromol. Chem.*, 1984; 185:9-18.
Kokubo et al., "A/W Glass Ceramics: Processing and Properties," *An Introduction to Bioceramics*, L.L. Hench & J. Wilson, Eds., World Scientific Publishing, Chapter 5, pp. 75-88, (1993).
Mazzaoui, et al. "Incorporation of Casein Phosphopeptide-Amorphous Calcium Phosphate into a Glass-ionomer Cement" *Journal of Dental Research*, Nov. 2003; 82(11):914-918.
McKenzie, *Advances in Protein Chemistry*, 22:75-135 (1967).
NSI Dental Pty Ltd., Hornsby Australia, Product Labeling, Dentacal Mouth Moistener, 1 page, use by 2005 on label.
NSI Dental Pty Ltd., Hornsby Australia, Topacal, C-5 Product Information and Supporting Publications, V4, May 2003.
NSI Dental Pty Ltd., Hornsby Australia, Topical C-5, Enamel Improving Cream, Product Packaging [ Undated], 1 page.
Product Advertisement, Recaldent, Victoria Australia, found in *Journal of Dental Research*, V. 84, No. 1, Jan. 2005, 1 page.
Product data sheet (i.e. sales or company literature): "AMCO—Casehesive™ Protein Polymers" datasheet. American Casein Company, Burlington, New Jersey, Oct. 3, 2001, 1 pg.
Product data sheet (i.e. sales or company literature): "AMCO—Edible Powdered Protein Products (p. 2)" datasheet [online]. American Casein Company, Burlington, New Jersey, Sep. 6, 2004 [retrieved on Feb. 9, 2005]. Retrieved from the Internet:<URL: http://www.americancasein.com/edible_2.htm>; 1 pg.
Product data sheet (i.e. sales or company literature): "AMCO—Protein Polymers for Technical Applications" (p. 1) datasheet [online]. American Casein Company, Burlington, New Jersey, Sep. 6, 2004 [retrieved on Feb. 9, 2005]. Retrieved from the Internet:<URL: http://www.americancasein.com/technical.htm>; 1 pg.
Product data sheet (i.e. sales or company literature): "American Casein Company—AMCO" datasheet [online]. American Casein Company, Burlington, New Jersey, Sep. 6, 2004 [retrieved on Feb. 9, 2005]. Retrieved from the Internet:<URL:http://www.americancasein.com>; 2pgs.
Product data sheet (i.e. sales or company literature): "Bone—replacement individually designed—3di Ltd." datasheet [online]. 3di Ltd., Saalbahnhofstr, Germany, [retrieved on Feb. 9, 2005]. Retrieved from the Internet:<URL:http://www.3di.de/_englisch/materialspezifika/material/htm>; 1 pg.
Product data sheet (i.e. sales or company literature): "Bone—replacement individually designed—3di Ltd." datasheet [online]. 3di Ltd., Saalbahnhofstr, Germany, [retrieved on Feb. 9, 2005]. Retrieved from the Internet:<URL: http://www.3di.de/_englisch/materialspezifika/biovert.htm>; 1 pg.
Product data sheet (i.e. sales or company literature): "Cerabone A-W Cerabone A-W Iliac Spacer", Nippon Electric Glass Co., Ltd, Shiga, Japan, 8 pages.
Product data sheet (i.e. sales or company literature): "Cerabone A-W Artificial Vertebrae, Intervertebral Spacer, Spinous Process Spacer," Nippon Electric Glass Co., Ltd, Shiga, Japan, 8 pages.
Product data sheet (i.e. sales or company literature): "Corporate Chronology Nippon Electric Glass 50 Years and Beyond" datasheet [online]. Nippon Electric Glass Co., Ltd., Otsu, Shiga, Japan, Aug. 1, 1998 [retrieved on Feb. 9, 2009]. Retrieved from the Internet:<URL:http://www.neg.co.jp/eng/company/history.html>; 4 pgs.
Product data sheet (i.e. sales or company literature): "NSI Dental—Manufacturer of dental restoratives for the dental practitioner" datasheet [online]. NSI Dental Pty Limited, Hornsby, Australia, [retrieved on Feb. 9, 2005]. Retrieved from the Internet:<URL:http://www.nsidental.com/>; 5 pgs.
Product data sheet (i.e. sales or company literature): "Revitalize Teeth! NovaMin Tooth Remineralization for Oral Care Products" datasheet [online]. NovaMin Technology Inc, Alachua, FL, [retrieved on Feb. 9, 2005]. Retrieved from the Internet:<URL: http://www.novamin.com/>; 1 pg.
Product data sheet (i.e. sales or company literature): "Welcome to Recaldent" datasheet [online]. Recaldent Pty Ltd, University of Melbourne, Australia, [retrieved on Feb. 9, 2005]. Retrieved from the Internet:<URL: http://www.recaldent.com/index.htm>; 1 pg.
Reynolds, et al. "Retention in Plaque and Remineralization of Enamel Lesions by Various Forms of Calcium in a Mouthrinse or Sugar-free Chewing Gum" *Journal of Dental Research*, Mar. 2003; 82(3):206-211.
Ribadeau Dumas et al. "Structure primaire de la caséine β bovine," *Eur. J. Biochem.*, 1972; 25:505-514. English language abstract.
Shen, et al. "Remineralization of Enamel Subsurface Lesions by Sugar-free Chewing Gum Containing Casein Phosphopeptide-Amorphous Calcium Phosphate" *Journal of Dental Research*, Dec. 2001; 80(12):2066-2070.
Skrtic et al., "Amorphous Calcium Phosphate-Based Bioactive Polymeric Composites for Mineralized Tissue Regeneration," *Journal of Research of the National Institute of Standards and Technology*, May-Jun. 2003; 108:167-182.
Tantbirojn, "Surface Modulation of Dental Hard Tissues," Ph.D. Thesis, University of MN, 234 pgs, (1998).
*The Merck Index, An Encyclopedia of Chemical, Drugs, and Biologicals*, Twelfth Edition, Merck & Co., Inc., Whitehouse Station, NJ, pp. 309-310, (1996).
Yamamuro, "A/W Glass Ceramics: Clinical Applications," *An Introduction to Bioceramics*, L.L. Hench & J. Wilson, Eds., World Scientific Publishing, Chapter 6, pp. 89-103, (1993).
Yli-Urpo et al., "Release of silica, calcium, phosphorus, and fluoride from glass ionomer cement containing bioactive glass" *Journal of Biomaterials Applications*, Jul. 2004, 19(1):5-20.
D'Andrea, "Covalent surface modification of calcium hydroxyapatite using n-alkyl and n-fluoroalkylphosphonic acids" Langmuir, 2003, vol. 19, No. 19, pp. 7904-7910.
Tanaka, "Surface modification of calcium hydroxyapatite with hexyl and decyl phosphates" Colloids and Surfaces A: Physicochemical and Engineering Aspects, May 1997, vol. 125, No. 1, pp. 53-62.

* cited by examiner

DENTAL FILLERS AND COMPOSITIONS INCLUDING PHOSPHATE SALTS

CROSS REFERENCE TO RELATED APPLICATIONS

This application is a national stage filing under 35 U.S.C. § 371 of PCT/US2005/040339, filed Nov. 7, 2005, which is a continuation of and claims priority to U.S. application Ser. No. 10/989,780, filed Nov. 16, 2004, the disclosure of which is incorporated by reference in its entirety herein.

BACKGROUND

Demineralization of dental structures is well known to lead to caries, decayed dentin, cementum, and/or enamel, conditions that typically require treatment with a dental restorative, for example. Although such conditions can usually be adequately treated using dental restoratives, restored dental structures oftentimes can be susceptible to further decay around the margins of the restoration.

The release of ions (e.g., calcium, and preferably calcium and phosphorus) into the oral environment is known to enhance the natural remineralizing capability of dental structures. It is believed that enhanced remineralization may be a useful supplement to, or even an alternative to, traditional dental restorative methods. However, known compositions that release calcium and phosphorus into the oral environment (e.g., calcium phosphate containing compositions) oftentimes lack desirable properties including, for example, sustained release capabilities.

Thus, new compositions capable of releasing ions (e.g., phosphorus and other ions) into the oral environment are needed.

SUMMARY OF THE INVENTION

In one aspect, the present invention provides a dental filler including a treated surface, and methods of making such a dental filler including a treated surface. The treated surface includes a phosphate salt represented by the formula:

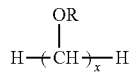

where x=2-4; each R is independently H or $P(O)(O^-)_2(M^{+n})_{2/n}$, with the proviso that at least one R group is $P(O)(O^-)_2(M^{+2n})_{2/n}$ and at least one R group is H; and M is a metal of valence n. Dental compositions including such a dental filler, and methods of using such dental compositions are also provided.

In another aspect, the present invention provides a dental composition including a hardenable resin and/or a water-dispersible, polymeric film former; and a phosphate salt of the formula:

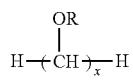

where x=2-4; each R is independently H or $P(O)(O^-)_2(M^{+n})_{2/1}$, with the proviso that at least one R group is $P(O)(O^-)_2(M^{+2n})_{2/n}$ and at least one R group is H; and M is a metal of valence n. Methods of using such dental compositions are also provided.

Dental fillers and compositions as disclosed herein preferably lead to enhanced remineralization of dental structures, which can offer potential benefits including, for example, the ability to remineralize enamel and/or dentin lesions; to occlude exposed dentin and/or cementum tubules which cause sensitivity; to recondition abraded and/or etched enamel surfaces; to reseal microleakage regions at interfaces; and to increase resistance of contacted and nearby tooth structures to acid attack.

Definitions

As used herein, "adhesive" or "dental adhesive" refers to a composition used as a pre-treatment on a dental structure (e.g., a tooth) to adhere a "dental material" (e.g., "restorative," an orthodontic appliance (e.g., bracket), or an "orthodontic adhesive") to the dental structure. An "orthodontic adhesive" refers to a highly (generally greater than 40% by weight) filled composition (more analogous to a "restorative material" than to a "dental adhesive") used to adhere an orthodontic appliance to a dental structure (e.g., tooth) surface. Generally, the dental structure surface is pre-treated, e.g., by etching, priming, and/or applying an adhesive to enhance the adhesion of the "orthodontic adhesive" to the dental structure surface.

As used herein, a "non-aqueous" composition (e.g., an adhesive) refers to a composition in which water has not been added as a component. However, there may be adventitious water in other components of the composition, but the total amount of water does not adversely affect stability (e.g., the shelf-life) of the non-aqueous composition. Non-aqueous compositions preferably include less than 1% by weight, more preferably less than 0.5% by weight, and most preferably less than 0.1% by weight water, based on the total weight of the non-aqueous composition.

As used herein, a "self-etching" composition refers to a composition that bonds to a dental structure surface without pretreating the dental structure surface with an etchant. Preferably, a self-etching composition can also function as a self-primer wherein no separate etchant or primer are used.

As used herein, a "self-adhesive" composition refers to a composition that is capable of bonding to a dental structure surface without pretreating the dental structure surface with a primer or bonding agent. Preferably, a self-adhesive composition is also a self-etching composition wherein no separate etchant is used.

As used herein, "hardening" or "curing" a composition are used interchangeably and refer to polymerization and/or crosslinking reactions including, for example, photopolymerization reactions and chemical polymerization techniques (e.g., ionic reactions reactions or chemical reactions forming radicals effective to polymerize ethylenically unsaturated compounds) involving one or more compounds capable of hardening or curing.

As used herein, a "dental structure surface" refers to tooth structures (e.g., enamel, dentin, and cementum) and bone.

As used herein, "dental material" refers to a material that may be bonded to a dental structure surface and includes, for example, dental restoratives, orthodontic appliances, and/or orthodontic adhesives.

As used herein, "(meth)acryl" is a shorthand term referring to "acryl" and/or "methacryl." For example, a "(meth) acryloxy" group is a shorthand term referring to either an acryloxy group (i.e., CH$_2$=CHC(O)O—) and/or a methacryloxy group (i.e., CH$_2$=C(CH$_3$)C(O)O—).

As used herein, an "amorphous" material is one which does not give rise to a discernible x-ray powder diffraction pattern. An "at least partially crystalline" material is one which gives rise to a discernible x-ray powder diffraction pattern.

As used herein, "groups" of the periodic table refer to and include groups 1-18 as defined in IUPAC Nomenclature of Inorganic Chemistry, Recommendations 1990.

As used herein, "a" or "an" means "at least one" or "one or more" unless otherwise indicated.

DETAILED DESCRIPTION OF PREFERRED EMBODIMENTS

The present invention provides dental fillers and/or compositions that include a phosphate salt. In some embodiments, a dental filler is provided that includes a treated surface that includes a phosphate salt. In some embodiments, dental compositions are provided that include such dental fillers. In some embodiments, dental compositions are provided that include a phosphate salt and a hardenable resin and/or a water-dispersible, polymeric film former. Methods of making and using such dental fillers and/or compositions are also provided.

Phosphate Salt

Phosphate salts useful in the present invention can be represented by the formula:

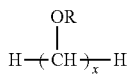

where x=2-4; each R is independently H or P(O)(O$^-$)$_2$(M$^{+n}$)$_{2/n}$, with the proviso that at least one R group is P(O)(O$^-$)$_2$(M$^{+2n}$)$_{2/n}$ and at least one R group is H; and M is a metal of valence n. Preferably x=3. In some embodiments, M is a Group 2 metal, a Group 3 metal, a transition metal, a Lanthanide, or a combination thereof. In some embodiments, M is Mg, Ca, Sr, Ba, Zn, Ag, Zr, Sn, or a combination thereof. In some preferred embodiments, M is Ca.

Exemplary phosphate salts as described herein include, for example, calcium glycerophosphate, zinc glycerophosphate, magnesium glycerophosphate, strontium glycerophosphate, tin glycerophosphate, zirconium glycerophosphate, and silver glycerophosphate. Preferred phosphate salts include calcium glycerophosphate.

Surface Treatment of Dental Fillers

Preferably, the dental fillers are surface treated by methods similar to those described, for example, in U.S. Pat. No. 5,332,429 (Mitra et al.). In brief, the dental fillers described herein can be surface treated by combining the filler with a liquid having dissolved, dispersed, or suspended therein, a phosphate salt as described herein. The liquid or additional liquids may optionally include additional surface treating agents (e.g., fluoride ion precursors, silanes, titanates, etc). Optionally, the liquid includes water, and if an aqueous liquid is used, it can be acidic or basic. Once treated, at least a portion of the liquid can be removed from the surface treated dental filler using any convenient technique (e.g., spray drying, oven drying, gap drying, lyophilizing, and combinations thereof). See, for example, U.S. Pat. No. 5,980,697 (Kolb et al.) for a description of gap drying. In one embodiment, the treated fillers can be oven dried, typically at drying temperatures of about 30° to about 100° C., for example, overnight. The surface treated filler can be further heated as desired. The treated and dried dental filler can then be screened or lightly comminuted to break up agglomerates. The resulting surface treated dental filler can be incorporated, for example, into a dental paste.

Dental fillers suitable for surface treatment can be selected from one or more of a wide variety of materials suitable for incorporation in compositions used for dental applications, such as fillers currently used in dental restorative compositions, and the like. Preferably the dental filler includes porous particles and/or porous agglomerates of particles. Preferred dental fillers include nanoparticles and/or agglomerates of nanoparticles. Preferred classes of fillers include metal oxides, metal fluorides, metal oxyfluorides, and combinations thereof, wherein the metal can be a heavy or non-heavy metal.

In preferred embodiments, the dental filler is an oxide, a fluoride, or an oxyfluoride of an element selected from the group consisting of Groups 2-5 elements, Groups 12-15 elements, Lanthanide elements, and combinations thereof. More preferably, the element is selected from the group consisting of Ca, Sr, Ba, Y, La, Ce, Pr, Nd, Pm, Sm Eu, Gd, Tb, Dy, Ho, Er, Tm Yb, Lu, Ti, Zr, Ta, Zn B, Al, Si, Sn, P, and combinations thereof. The dental filler can be a glass, an amorphous material, or a crystalline material. Optionally, the dental filler can include a source of fluoride ions. Such dental fillers include, for example, fluoroaluminosilicate glasses.

The filler is preferably finely divided. The filler can have a unimodial or polymodial (e.g., bimodal) particle size distribution. Preferably, the maximum particle size (the largest dimension of a particle, typically, the diameter) of the filler is less than 20 micrometers, more preferably less than 10 micrometers, and most preferably less than 5 micrometers. Preferably, the average particle size of the filler is less than 2 micrometers, more preferably less than 0.1 micrometers, and most preferably less than 0.075 micrometer.

The filler can be an inorganic material. It can also be a crosslinked organic material that is insoluble in the resin system, and is optionally filled with inorganic filler. The filler should in any event be nontoxic and suitable for use in the mouth. The filler can be radiopaque or radiolucent. The filler typically is substantially insoluble in water.

Examples of suitable inorganic fillers are naturally occurring or synthetic materials including, but not limited to: quartz; nitrides (e.g., silicon nitride); glasses derived from, for example, Zr, Sr, Ce, Sb, Sn, Ba, Zn, and Al; feldspar; borosilicate glass; kaolin; talc; titania; low Mohs hardness fillers such as those described in U.S. Pat. No. 4,695,251 (Randklev); and submicron silica particles (e.g., pyrogenic silicas such as those available under the trade designations AEROSIL, including "OX 50," "130," "150" and "200" silicas from Degussa Corp., Akron, Ohio and CAB-O-SIL M5 silica from Cabot Corp., Tuscola, Ill.). Examples of suitable organic filler particles include filled or unfilled pulverized polycarbonates, polyepoxides, and the like.

Preferred non-acid-reactive filler particles are quartz, submicron silica, and non-vitreous microparticles of the type described in U.S. Pat. No. 4,503,169 (Randklev). Mixtures of these non-acid-reactive fillers are also contemplated, as well as combination fillers made from organic and inorganic materials. Silane-treated zirconia-silica (Zr—Si) filler is especially preferred in certain embodiments.

The filler can also be an acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. FAS glasses are particularly preferred. The FAS glass typically contains sufficient elutable cations so that a hardened dental composition will form when the glass is mixed with the components of the hardenable composition. The glass also typically contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than about 12 micrometers, typically no greater than 10 micrometers, and more typically no greater than 5 micrometers as measured using, for example, a sedimentation analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

Other suitable fillers are disclosed, for example, in U.S. Pat. No. 6,306,926 (Bretscher et al.), U.S. Pat. No. 6,387,981 (Zhang et al.), U.S. Pat. No. 6,572,693 (Wu et al.), and U.S. Pat. No. 6,730,156 (Windisch et al.), as well as International Publication Nos. WO 01/30307 (Zhang et al.) and WO 03/063804 (Wu et al.). Filler components described in these references include nanosized silica particles, nanosized metal oxide particles, and combinations thereof. Nanofillers are also described in U.S. patent application Ser. Nos. 10/847,781; 10/847,782; and 10/847,803; all three of which were filed on May 17, 2004.

The surface treated dental filler preferably includes at least 0.01%, more preferably at least 0.05%, and most preferably at least 0.1% by weight phosphate salt, based on the total dry weight of the dental filler (i.e., excluding the liquid used in the treatment). The surface treated dental filler preferably includes at most 50%, more preferably at most 30%, and most preferably at most 20% by weight phosphate salt, based on the total dry weight of the dental filler (i.e., excluding the liquid used in the treatment).

For some embodiments of the present invention that include surface treated dental filler (e.g., dental adhesive compositions), the compositions preferably include at least 1% by weight, more preferably at least 2% by weight, and most preferably at least 5% by weight surface treated dental filler, based on the total weight of the composition. For such embodiments, compositions of the present invention preferably include at most 40% by weight, more preferably at most 20% by weight, and most preferably at most 15% by weight surface treated dental filler, based on the total weight of the composition.

For other embodiments (e.g., wherein the composition is a dental restorative or an orthodontic adhesive), compositions of the present invention preferably include at least 40% by weight, more preferably at least 45% by weight, and most preferably at least 50% by weight surface treated dental filler, based on the total weight of the composition. For such embodiments, compositions of the present invention preferably include at most 90% by weight, more preferably at most 80% by weight, even more preferably at most 70% by weight, and most preferably at most 50% by weight surface treated dental filler, based on the total weight of the composition.

Optionally, the treated surface of the dental filler can further include a silane (e.g., as described, for example, in U.S. Pat. No. 5,332,429 (Mitra et al.)), an antibacterial agent (e.g., chlorhexidine; quaternary ammonium salts; metal containing compounds such as Ag, Sn, or Zn containing compounds; and combinations thereof), and/or a source of fluoride ions (e.g., fluoride salts, fluoride containing glasses, fluoride containing compounds, and combinations thereof).

Dental Compositions Including a Phosphate Salt

In some embodiments, the present invention provides dental compositions that include a phosphate salt and a hardenable resin and/or a water-dispersible, polymeric film former. Such dental compositions can be prepared either directly (e.g., by combining the phosphate salt with the hardenable resin or the water-dispersible, polymeric film former) or indirectly (e.g., by generating the phosphate salt in the hardenable resin or a water-dispersible, polymeric film former in situ). Suitable in situ methods of generating the phosphate salt include, for example, acid neutralizations and/or cation exchange reactions.

Dental compositions that include a phosphate salt in a hardenable resin include, for example, dental adhesives, dental restoratives, and orthodontic adhesives. Dental compositions that include a phosphate salt in a water-dispersible, polymeric film former include, for example, coatings, varnishes, sealants, primers, and desensitizers. In some embodiments as described herein above, the phosphate salt is present in a surface treated filler. In other embodiments, the phosphate salt is not present in a surface treated filler.

For embodiments in which a dental composition includes a phosphate salt in a hardenable resin, wherein the phosphate salt is not present in a surface treated filler, the dental composition preferably includes at least 0.01%, more preferably at least 0.1%, and most preferably at least 1% by weight phosphate salt, based on the total weight of the dental composition. For such embodiments, the dental composition preferably includes at most 70%, more preferably at most 50%, and most preferably at most 25% by weight phosphate salt, based on the total weight of the dental composition.

For embodiments in which a dental composition includes a phosphate salt in a water-dispersible, polymeric film former, wherein the phosphate salt is not present in a surface treated filler, the dental composition preferably includes at least 0.01%, more preferably at least 0.1%, and most preferably at least 1% by weight phosphate salt, based on the total weight of the dental composition. For such embodiments, the dental composition preferably includes at most 70%, more preferably at most 50%, and most preferably at most 25% by weight phosphate salt, based on the total weight of the dental composition.

Dental compositions of the present invention can also include optional additives as described herein below.

Dental compositions as described herein can be useful as dental primers, dental adhesives, cavity liners, cavity cleansing agents, cements, coatings, varnishes, orthodontic adhesives, restoratives, sealants, desensitizers, and combinations thereof.

Dental Compositions Including Hardenable Resins

Dental compositions of the present invention are useful for treating hard surfaces, preferably, hard tissues such as dentin, enamel, and bone. Such dental compositions can be aqueous or non-aqueous. In some embodiments, the compositions can be hardened (e.g., polymerized by conventional photopolymerization and/or chemical polymerization techniques) prior to applying the dental material. In other embodiments, the compositions can be hardened (e.g., polymerized by conventional photopolymerization and/or chemical polymerization techniques) after applying the dental material.

Suitable photopolymerizable compositions that can be used as dental materials and dental adhesive compositions in methods of the present invention can include epoxy resins (which contain cationically active epoxy groups), vinyl ether resins (which contain cationically active vinyl ether groups), ethylenically unsaturated compounds (which contain free radically active unsaturated groups, e.g., acrylates and methacrylates), and combinations thereof. Also suitable are polymerizable materials that contain both a cationically active functional group and a free radically active functional group in a single compound. Examples include epoxy-functional (meth)acrylates.

Ethylenically Unsaturated Compounds with Acid Functionality

As used herein, ethylenically unsaturated compounds with acid functionality is meant to include monomers, oligomers, and polymers having ethylenic unsaturation and acid and/or acid-precursor functionality. Acid-precursor functionalities include, for example, anhydrides, acid halides, and pyrophosphates.

Ethylenically unsaturated compounds with acid functionality include, for example, α,β-unsaturated acidic compounds such as glycerol phosphate mono(meth)acrylates, glycerol phosphate di(meth)acrylates, hydroxyethyl(meth) acrylate (e.g., HEMA) phosphates, bis((meth)acryloxyethyl) phosphate, ((meth)acryloxypropyl) phosphate, bis((meth) acryloxypropyl) phosphate, bis((meth)acryloxy)propyloxy phosphate, (meth)acryloxyhexyl phosphate, bis((meth)acryloxyhexyl) phosphate, (meth)acryloxyoctyl phosphate, bis ((meth)acryloxyoctyl) phosphate, (meth)acryloxydecyl phosphate, bis((meth)acryloxydecyl) phosphate, caprolactone methacrylate phosphate, citric acid di- or tri-methacrylates, poly(meth)acrylated oligomaleic acid, poly(meth) acrylated polymaleic acid, poly(meth)acrylated poly(meth) acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like, may be used as components in the hardenable resin system. Also monomers, oligomers, and polymers of unsaturated carbonic acids such as (meth)acrylic acids, aromatic (meth) acrylated acids (e.g., methacrylated trimellitic acids), and anhydrides thereof can be used. Certain preferred compositions of the present invention include an ethylenically unsaturated compound with acid functionality having at least one P—OH moiety.

Certain of these compounds are obtained, for example, as reaction products between isocyanatoalkyl(meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. Mixtures of such compounds can be used if desired.

Additional ethylenically unsaturated compounds with acid functionality include, for example, polymerizable bisphosphonic acids as disclosed for example, in U.S. Provisional Application No. 60/437,106, filed Dec. 30, 2002; AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and European Pat. Application Publication Nos. EP 712,622 (Tokuyama Corp.) and EP 1,051,961 (Kuraray Co., Ltd.).

Compositions of the present invention can also include combinations of ethylenically unsaturated compounds with acid functionality as described, for example, in U.S. Provisional Application Ser. No. 60/600,658, filed on Aug. 11, 2004.

Preferably, the compositions of the present invention include at least 1% by weight, more preferably at least 3% by weight, and most preferably at least 5% by weight ethylenically unsaturated compounds with acid functionality, based on the total weight of the unfilled composition. Preferably, compositions of the present invention include at most 80% by weight, more preferably at most 70% by weight, and most preferably at most 60% by weight ethylenically unsaturated compounds with acid functionality, based on the total weight of the unfilled composition.

Ethylenically Unsaturated Compounds without Acid Functionality

The compositions of the present invention may also include one or more polymerizable components in addition to the ethylenically unsaturated compounds with acid functionality, thereby forming hardenable compositions. The polymerizable components may be monomers, oligomers, or polymers.

In certain embodiments, the compositions are photopolymerizable, i.e., the compositions contain a photopolymerizable component and a photoinitiator (i.e., a photoinitiator system) that upon irradiation with actinic radiation initiates the polymerization (or hardening) of the composition. Such photopolymerizable compositions can be free radically polymerizable.

In certain embodiments, the compositions are chemically polymerizable, i.e., the compositions contain a chemically polymerizable component and a chemical initiator (i.e., initiator system) that can polymerize, cure, or otherwise harden the composition without dependence on irradiation with actinic radiation. Such chemically polymerizable compositions are sometimes referred to as "self-cure" compositions and may include glass ionomer cements, resin-modified glass ionomer cements, redox cure systems, and combinations thereof.

Preferably, compositions of the present invention include at least 5% by weight, more preferably at least 10% by weight, and most preferably at least 15% by weight ethylenically unsaturated compounds without acid functionality, based on the total weight of the unfilled composition. Preferably, compositions of the present invention include at most 95% by weight, more preferably at most 90% by weight, and most preferably at most 80% by weight ethylenically unsaturated compounds without acid functionality, based on the total weight of the unfilled composition.

Photopolymerizable Compositions

Suitable photopolymerizable compositions may include photopolymerizable components (e.g., compounds) that include ethylenically unsaturated compounds (which contain free radically active unsaturated groups). Examples of useful ethylenically unsaturated compounds include acrylic acid esters, methacrylic acid esters, hydroxy-functional acrylic acid esters, hydroxy-functional methacrylic acid esters, and combinations thereof.

Photopolymerizable compositions may include compounds having free radically active functional groups that may include monomers, oligomers, and polymers having one or more ethylenically unsaturated group. Suitable compounds contain at least one ethylenically unsaturated bond and are capable of undergoing addition polymerization. Such free radically polymerizable compounds include mono-, di- or poly-(meth)acrylates (i.e., acrylates and methacrylates) such as, methyl(meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl(meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenolA di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500), copolymerizable mixtures of acrylated monomers such as those in U.S. Pat. No. 4,652,274 (Boettcher et al.), acrylated oligomers such as those of U.S. Pat. No. 4,642,126 (Zador et al.), and poly(ethylenically unsaturated) carbamoyl isocyanurates such as those disclosed in U.S. Pat. No. 4,648,843 (Mitra); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth)acrylates as disclosed, for example, in U.S. Pat. No. 5,076,844 (Fock et al.), U.S. Pat. No. 4,356,296 (Griffith et al.), EP-0373 384 (Wagenknecht et al.), EP-0201 031 (Reiners et al.), and EP-0201 778 (Reiners et al.). Mixtures of two or more free radically polymerizable compounds can be used if desired.

The polymerizable component may also contain hydroxyl groups and free radically active functional groups in a single molecule. Examples of such materials include hydroxyalkyl (meth)acrylates, such as 2-hydroxyethyl(meth)acrylate and 2-hydroxypropyl(meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-methacryloxypropoxy)phenyl]propane (bisGMA). Suitable ethylenically unsaturated compounds are also available from a wide variety of commercial sources, such as Sigma-Aldrich, St. Louis. Mixtures of ethylenically unsaturated compounds can be used if desired.

In certain embodiments photopolymerizable components include PEGDMA (polyethyleneglycol dimethacrylate having a molecular weight of approximately 400), bisGMA, UDMA (urethane dimethacrylate), GDMA (glycerol dimethacrylate), TEGDMA (triethyleneglycol dimethacrylate), bisEMA6 as described in U.S. Pat. No. 6,030,606 (Holmes), and NPGDMA (neopentylglycol dimethacrylate). Various combinations of the polymerizable components can be used if desired.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Preferred iodonium salts are the diaryl iodonium salts, e.g., diphenyliodonium chloride, diphenyliodonium hexafluorophosphate, diphenyliodonium tetrafluoroborate, and tolylcumyliodonium tetrakis(pentafluorophenyl)borate. Preferred photosensitizers are monoketones and diketones that absorb some light within a range of 400 nm to 520 nm (preferably, 450 nm to 500 nm). More preferred compounds are alpha diketones that have some light absorption within a range of 400 nm to 520 nm (even more preferably, 450 to 500 nm). Preferred compounds are camphorquinone, benzil, furil, 3,3,6,6-tetramethylcyclohexanedione, phenanthraquinone, 1-phenyl-1,2-propanedione and other 1-aryl-2-alkyl-1,2-ethanediones, and cyclic alpha diketones. Most preferred is camphorquinone. Preferred electron donor compounds include substituted amines, e.g., ethyl dimethylaminobenzoate. Other suitable tertiary photoinitiator systems useful for photopolymerizing cationically polymerizable resins are described, for example, in U.S. Pat. Publication No. 2003/0166737 (Dede et al.).

Other suitable photoinitiators for polymerizing free radically photopolymerizable compositions include the class of phosphine oxides that typically have a functional wavelength range of 380 nm to 1200 nm. Preferred phosphine oxide free radical initiators with a functional wavelength range of 380 nm to 450 mm are acyl and bisacyl phosphine oxides such as those described in U.S. Pat. No. 4,298,738 (Lechtken et al.), U.S. Pat. No. 4,324,744 (Lechtken et al.), U.S. Pat. No. 4,385,109 (Lechtken et al.), U.S. Pat. No. 4,710,523 (Lechtken et al.), and U.S. Pat. No. 4,737,593 (Ellrich et al.), U.S. Pat. No. 6,251,963 (Kohler et al.); and EP Application No. 0 173 567 A2 (Ying).

Commercially available phosphine oxide photoinitiators capable of free-radical initiation when irradiated at wavelength ranges of greater than 380 nm to 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Typically, the phosphine oxide initiator is present in the photopolymerizable composition in catalytically effective amounts, such as from 0.1 weight percent to 5.0 weight percent, based on the total weight of the composition.

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. When present, the amine reducing agent is present in the photopolymerizable composition in an amount from 0.1 weight percent to 5.0 weight percent, based on the total weight of the composition. Useful amounts of other initiators are well known to those of skill in the art.

Chemically Polymerizable Compositions

The chemically polymerizable compositions may include redox cure systems that include a polymerizable component (e.g., an ethylenically unsaturated polymerizable component) and redox agents that include an oxidizing agent and a reducing agent. Suitable polymerizable components, redox agents, optional acid-functional components, and optional fillers that are useful in the present invention are described in U.S. Pat. Publication Nos. 2003/0166740 (Mitra et al.) and 2003/0195273 (Mitra et al.).

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions. They should be sufficiently miscible with the resin system (and preferably water-soluble) to permit ready dissolution in (and discourage separation from) the other components of the polymerizable composition.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. In some embodiments it may be preferred to include a secondary ionic salt to enhance the stability of the polymerizable composition as described in U.S. Pat. Publication No. 2003/0195273 (Mitra et al.).

The reducing and oxidizing agents are present in amounts sufficient to permit an adequate free-radical reaction rate. This can be evaluated by combining all of the ingredients of the polymerizable composition except for the optional filler, and observing whether or not a hardened mass is obtained.

Preferably, the reducing agent is present in an amount of at least 0.01% by weight, and more preferably at least 0.1% by weight, based on the total weight (including water) of the components of the polymerizable composition. Preferably, the reducing agent is present in an amount of no greater than 10% by weight, and more preferably no greater than 5% by weight, based on the total weight (including water) of the components of the polymerizable composition.

Preferably, the oxidizing agent is present in an amount of at least 0.01% by weight, and more preferably at least 0.10% by weight, based on the total weight (including water) of the components of the polymerizable composition. Preferably, the oxidizing agent is present in an amount of no greater than 10% by weight, and more preferably no greater than 5% by weight, based on the total weight (including water) of the components of the polymerizable composition.

The reducing or oxidizing agents can be microencapsulated as described in U.S. Pat. No. 5,154,762 (Mitra et al.). This will generally enhance shelf stability of the polymerizable composition, and if necessary permit packaging the reducing and oxidizing agents together. For example, through appropriate selection of an encapsulant, the oxidizing and reducing agents can be combined with an acid-functional component and optional filler and kept in a storage-stable state. Likewise, through appropriate selection of a water-insoluble encapsulant, the reducing and oxidizing agents can be combined with an FAS glass and water and maintained in a storage-stable state.

A redox cure system can be combined with other cure systems, e.g., with a photopolymerizable composition such as described U.S. Pat. No. 5,154,762 (Mitra et al.).

In some embodiments, dental compositions of the present invention including a hardenable resin can be hardened to fabricate a dental article selected from the group consisting of crowns, fillings, mill blanks, orthodontic devices, and prostheses.

Water-Dispersible Polymeric Film Former

In some embodiments, water-dispersible polymeric film formers as disclosed herein include a repeating unit that includes a polar or polarizable group as described herein below. In certain embodiments, the water-dispersible polymeric film formers also include a repeating unit that includes a fluoride releasing group, a repeating unit that includes a hydrophobic hydrocarbon group, a repeating unit that includes a graft polysiloxane chain, a repeating unit that includes a hydrophobic fluorine-containing group, a repeating unit that includes a modulating group, or combinations thereof, as described herein below. In some embodiments, the polymer optionally includes a reactive group (e.g., ethylenically unsaturated groups, epoxy groups, or silane moieties capable of undergoing a condensation reaction). Exemplary water-dispersible polymeric film formers are disclosed, for example, in U.S. Pat. No. 5,468,477 (Kumar et al.), U.S. Pat. No. 5,525,648 (Aasen et al.), U.S. Pat. No. 5,607,663 (Rozzi et al.), U.S. Pat. No. 5,662,887 (Rozzi et al.), U.S. Pat. No. 5,725,882 (Kumar et al.), U.S. Pat. No. 5,866,630 (Mitra et al.), U.S. Pat. No. 5,876,208 (Mitra et al.), U.S. Pat. No. 5,888,491 (Mitra et al.), and U.S. Pat. No. 6,312,668 (Mitra et al.).

Repeating units including a polar or polarizable group are derived from vinylic monomers such as acrylates, methacrylates, crotonates, itaconates, and the like. The polar groups can be acidic, basic or salt. These groups can also be ionic or neutral.

Examples of polar or polarizable groups include neutral groups such as hydroxy, thio, substituted and unsubstituted amido, cyclic ethers (such as oxanes, oxetanes, furans and pyrans), basic groups (such as phosphines and amines, including primary, secondary, tertiary amines), acidic groups (such as oxy acids, and thiooxyacids of C, S, P, B), ionic groups (such as quarternary ammonium, carboxylate salt, sulfonic acid salt and the like), and the precursors and protected forms of these groups. Additionally, a polar or polarizable group could be a macromonomer. More specific examples of such groups follow.

Polar or polarizable groups may be derived from mono- or multifunctional carboxyl group containing molecules represented by the general formula:

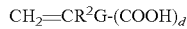

$$CH_2=CR^2G\text{-}(COOH)_d$$

where $R^2$=H, methyl, ethyl, cyano, carboxy or carboxymethyl, d=1-5 and G is a bond or a hydrocarbyl radical linking group containing from 1-12 carbon atoms of valence d+1 and optionally substituted with and/or interrupted with a substituted or unsubstituted heteroatom (such as O, S, N and P). Optionally, this unit may be provided in its salt form. The preferred monomers in this class are acrylic acid, methacrylic acid, itaconic acid, and N-acryloyl glycine.

Polar or polarizable groups may, for example, be derived from mono- or multifunctional hydroxy group containing molecules represented by the general formula:

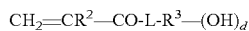

$$CH_2=CR^2\text{—}CO\text{-}L\text{-}R^3\text{—}(OH)_d$$

where $R^2$=H, methyl, ethyl, cyano, carboxy or carboxyalkyl, L=O, NH, d=1-5 and $R^3$ is a hydrocarbyl radical of valence d+1 containing from 1-12 carbon atoms. The preferred monomers in this class are hydroxyethyl(meth)acrylate, hydroxypropyl(meth)acrylate, hydroxybutyl(meth)acrylate, glycerol mono(meth)acrylate, tris(hydroxymethyl) ethane monoacrylate, pentaerythritol mono(meth)acrylate, N-hydroxymethyl(meth)acrylamide, hydroxyethyl(meth)acrylamide, and hydroxypropyl(meth)acrylamide.

Polar or polarizable groups may alternatively be derived from mono- or multifunctional amino group containing molecules of the general formula:

$$CH_2=CR^2\text{—}CO\text{-}L\text{-}R^3\text{—}(NR^4R^5)_d$$

where $R^2$, L, $R^3$, and d are as defined above and $R^4$ and $R^5$ are H or alkyl groups of 1-12 carbon atoms or together they constitute a carbocyclic or heterocyclic group. Preferred monomers of this class are aminoethyl(meth)acrylate, aminopropyl(meth)acrylate, N,N-dimethylaminoethyl (meth)acrylate, N,N-diethylaminoethyl(meth)acrylate, N,N-dimethylaminopropyl (meth)acrylamide, N-isopropylaminopropyl(meth)acrylamide, and 4-methyl-1-acryloyl-piperazine.

Polar or polarizable groups may also be derived from alkoxy substituted (meth)acrylates or (meth)acrylamides such as methoxyethyl(meth)acrylate, 2-(2-ethoxyethoxy) ethyl(meth)acrylate, polyethylene glycol mono(meth)acrylate or polypropylene glycol mono(meth)acrylate.

Polar or polarizable groups units may be derived from substituted or unsubstituted ammonium monomers of the general formula:

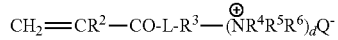

$$CH_2=CR^2\text{—}CO\text{-}L\text{-}R^3\text{—}(\overset{\oplus}{N}R^4R^5R^6)_dQ^-$$

where $R^2$, $R^3$, $R^4$, $R^5$, L and d are as defined above, and where $R^6$ is H or alkyl of 1-12 carbon atoms and $Q^-$ is an organic or inorganic anion. Preferred examples of such monomers include 2-N,N,N-trimethylammonium ethyl (meth)acrylate, 2-N,N,N-triethylammonium ethyl(meth) acrylate, 3-N,N,N-trimethylammonium propyl (meth)acrylate, N(2-N',N',N'-trimethylammonium)ethyl(meth) acrylamide, N-(dimethyl hydroxyethyl ammonium)propyl (meth)acrylamide, or combinations thereof, where the counterion may include fluoride, chloride, bromide, acetate, propionate, laurate, palmitate, stearate, or combinations thereof. The monomer can also be N,N-dimethyl diallyl ammonium salt of an organic or inorganic counterion.

Ammonium group containing polymers can also be prepared by using as the polar or polarizable group any of the amino group containing monomer described above, and acidifying the resultant polymers with organic or inorganic acid to a pH where the pendant amino groups are substantially protonated. Totally substituted ammonium group containing polymers may be prepared by alkylating the above described amino polymers with alkylating groups, the method being commonly known in the art as the Menschutkin reaction.

Polar or polarizable groups can also be derived from sulfonic acid group containing monomers, such as vinyl sulfonic acid, styrene sulfonic acid, 2-acrylamido-2-methyl propane sulfonic acid, allyloxybenzene sulfonic acid, and the like. Alternatively, polar or polarizable groups may be derived from phosphorous acid or boron acid group-containing monomers. These monomers may be used in the protonated acid form as monomers and the corresponding polymers obtained may be neutralized with an organic or inorganic base to give the salt form of the polymers.

Preferred repeating units of a polar or polarizable group include acrylic acid, itaconic acid, N-isopropylacrylamide, or combinations thereof.

In certain embodiments, the water-dispersible polymeric film formers disclosed herein also include a repeating unit that includes a fluoride releasing group. A preferred fluoride releasing group includes tetrafluoroborate anions as disclosed, for example, in U.S. Pat. No. 4,871,786 (Aasen et al.). A preferred repeating unit of a fluoride releasing group includes trimethylammoniummethyl methacrylate.

In certain embodiments, the water-dispersible polymeric film formers disclosed herein also include a repeating unit that includes a hydrophobic hydrocarbon group. An exemplary hydrophobic hydrocarbon group is derived from an ethylenically unsaturated preformed hydrocarbon moiety having a weight average molecular weight greater than 160. Preferably the hydrocarbon moiety has a molecular weight of at least 160. Preferably the hydrocarbon moiety has a molecular weight of at most 100,000, and more preferably at most 20,000. The hydrocarbon moiety may be aromatic or non-aromatic in nature, and optionally may contain partially or fully saturated rings. Preferred hydrophobic hydrocarbon moieties are dodecyl and octadecyl acrylates and methacrylates. Other preferred hydrophobic hydrocarbon moieties include macromonomers of the desired molecular weights prepared from polymerizable hydrocarbons, such as ethylene, styrene, alpha-methyl styrene, vinyltoluene, and methyl methacrylate.

In certain embodiments, the water-dispersible polymeric film formers disclosed herein also include a repeating unit that includes a hydrophobic fluorine containing group. Exemplary repeating units of hydrophobic fluorine-containing groups include acrylic or methacrylic acid esters of 1,1-dihydroperfluoroalkanols and homologs: $CF_3(CF_2)_xCH_2OH$ and $CF_3(CF_2)_x(CH_2)_yOH$, where x is zero to 20 and y is at least 1 up to 10; ω-hydrofluoroalkanols $(HCF_2(CF_2)_x(CH_2)_yOH)$, where x is 0 to 20 and y is at least 1 up to 10; fluoroalkylsulfonamido alcohols; cyclic fluoroalkyl alcohols; and $CF_3(CF_2CF_2O)_q(CF_2O)_x(CH_2)_yOH$, where q is 2 to 20 and greater than x, x is 0 to 20, and y is at least 1 up to 10.

Preferred repeating units of a hydrophobic fluorine-containing group include 2-(methyl(nonafluorobutyl)sulfonyl) amino)ethyl acrylate, 2-(methyl(nonafluorobutyl)sulfonyl) amino)ethyl methacrylate, or combinations thereof.

In certain embodiments, the water-dispersible polymeric film formers disclosed herein also include a repeating unit that includes a graft polysiloxane chain. The graft polysiloxane chain is derived from an ethylenically unsaturated preformed organosiloxane chain. The molecular weight of this unit is generally above 500. Preferred repeating units of a graft polysiloxane chain include a silicone macromer.

Monomers used to provide the graft polysiloxane chain of this invention are terminally functional polymers having a single functional group (vinyl, ethylenically unsaturated, acryloyl, or methacryloyl group) and are sometimes termed macromonomers or "macromers". Such monomers are known and may be prepared by methods as disclosed, for example, in U.S. Pat. No. 3,786,116 (Milkovich et al.) and U.S. Pat. No. 3,842,059 (Milkovich et al.). The preparation of polydimethylsiloxane macromonomer and subsequent copolymerization with vinyl monomer have been described in several papers by Y. Yamashita et al., [Polymer J. 14, 913 (1982); ACS Polymer Preprints 25 (1), 245 (1984); Makromol. Chem. 185, 9 (1984)].

In certain embodiments, the water-dispersible polymeric film formers disclosed herein also include a repeating unit that includes a modulating group. Exemplary modulating groups are derived from acrylate or methacrylate or other vinyl polymerizable starting monomers and optionally contain functionalities that modulate properties such as glass transition temperature, solubility in the carrier medium, hydrophilic-hydrophobic balance and the like.

Examples of modulating groups include the lower to intermediate methacrylic acid esters of 1-12 carbon straight, branched or cyclic alcohols. Other examples of modulating groups include styrene, vinyl esters, vinyl chloride, vinylidene chloride, acryloyl monomers and the like.

Preferred film formers are acrylate-based copolymers and urethane polymers such as the AVALURE series of compounds (e.g., AC-315 and UR-450), and carbomer-based polymers such as the CARBOPOL series of polymers (e.g., 940NF), all available from Noveon, Inc., Cleveland, Ohio.

Optional Additives

Optionally, compositions of the present invention may contain solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), and water.

If desired, the compositions of the invention can contain additives such as indicators, dyes, pigments, inhibitors, accelerators, viscosity modifiers, wetting agents, tartaric acid, chelating agents, buffering agents, stabilizers, and other similar ingredients that will be apparent to those skilled in the art. Additionally, medicaments or other therapeutic substances can be optionally added to the dental compositions. Examples include, but are not limited to, fluoride sources, whitening agents, anticaries agents (e.g., xylitol), calcium sources, phosphorus sources, remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents, antifungal agents, agents for treating xerostomia, desensitizers, and the like, of the type often used in dental compositions. Combination of any of the above additives may also be employed. The selection and amount of any one such additive can be selected by one of skill in the art to accomplish the desired result without undue experimentation.

Methods of Use

Exemplary methods of using compositions of the present invention are described in the Examples. In some embodiments of the present invention, dental compositions of the present invention can be contacted with a tooth structure to treat the tooth structure. In some embodiments, placing a dental composition according to the present invention in an oral environment can effect remineralization, reduction of sensitivity, and/or protection of the tooth structure. In preferred embodiments, placing a dental composition according to the present invention in an oral environment delivers ions (e.g., calcium, phosphorus, and/or fluorine containing ions) to the oral environment.

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is deionized water, and all molecular weights are weight average molecular weight.

EXAMPLES

Test Methods

Compressive Strength (CS) Test Method

Compressive strength of a test sample was measured according to ANSI/ASA specification No. 27 (1993). A sample was packed into a 4-mm (inside diameter) glass tube; the tube was capped with silicone rubber plugs; and then the tube was compressed axially at approximately 0.28 MPa for 5 minutes. The sample was then light cured for 90 seconds by exposure to two oppositely disposed VISILUX Model 2500 blue light guns (3M Co., St. Paul, Minn.), followed by irradiation for 180 seconds in a Dentacolor XS unit (Kulzer, Inc., Germany). Cured samples were cut with a diamond saw to form 8-mm long cylindrical plugs for measurement of compressive strength. The plugs were stored in distilled water at 37° C. for 24 hours prior to testing. Measurements were carried out on an Instron tester (Instron 4505, Instron Corp., Canton, Mass.) with a 10 kilonewton (kN) load cell at a crosshead speed of 1 mm/minute. Five cylinders of cured samples were prepared and measured with the results reported in MPa as the average of the five measurements.

Diametral Tensile Strength (DTS) Test Method

Diametral tensile strength of a test sample was measured according to ANSI/ASA specification No. 27 (1993). Samples were prepared as described for the CS Test Method, except that the cured samples were then cut into 2.2-mm thick disks for measurement of DTS. The disks were stored in water as described above and measured with an Instron tester (Instron 4505, Instron Corp.) with a 10 (kN) load cell at a crosshead speed of 1 mm/minute. Five disks of cured samples were prepared and measured with results reported in MPa as the average of the five measurements.

Work Time (WT) Test Method

The working time for a mixed cement to solidify was measured according to the following procedure. The tools and pastes were stored before use in a constant temperature and humidity room (22° C. and 50% RH) and the procedure was conducted in the same room. Selected amounts of A and B pastes were mixed by a spatula on a pad for 25 seconds (sec) and the resulting mixed composition sample transferred into the semi-cylindrical trough section (8-cm long, 1-cm wide and 3-mm deep) of an 8-cm by 10-cm plastic block. At time 1:00 min, perpendicular grooves were made using a ball point (1-mm diameter) groove maker across the trough every 30 sec; at 2:00 min, the grooves were made every 15 sec; and, closer to the end of the working time, the grooves were made every 10 sec. The end of the working time was determined when the lumps of the cement sample moved with the groove maker. The working time was reported as the average of 2 or 3 measurements.

Spectral Opacity (SO) Test Method

ASTM-D2805-95 was modified to measure the spectral opacity for dental materials with thicknesses of approximately 1.0 mm. Disk-shaped, 1-mm thick by 20-mm diameter samples were cured by exposing them to illumination from a 3M Visilux-2 dental curing light for 60 seconds on each side of the disk at a distance of 6 mm. Y-tristimulus values for the disks were measured on an Ultrascan XE Colorimeter with a ⅜ inch aperture (Hunter Associates Labs, Reston, Va.) with separate white and black backgrounds. The D65 Illuminant was used with no filters for all measurements. A 10-degree angle of view was used. The Y-tristimulus values for the white and black substrates were 85.28 and 5.35, respectively. The spectral opacity is calculated as the ratio of the reflectance of a material on a black substrate to that of an identical material on a white substrate. Reflectance is defined as equal to the Y-tristimulus value. Thus, spectral opacity=$R_B/R_W$, where $R_B$=reflectance of a disk on a black substrate and $R_w$=reflectance of the same disk on a white substrate. Spectral opacity is unitless. Lower spectral opacity values indicate lower visual opacity and greater translucency of a material.

Visual Opacity (MacBeth Values) Test Method

Disc-shaped (1-mm thick×15-mm diameter) paste samples were cured by exposing them to illumination from a VISILUX 2 curing light (3M Company, St. Paul, Minn.) for 60 seconds on each side of the disk at a distance of 6 mm. Hardened samples were measured for direct light transmission by measuring transmission of light through the thickness of the disk using a MacBeth transmission densitometer Model TD-903 equipped with a visible light filter, available from MacBeth (MacBeth, Newburgh, N.Y.). Lower MacBeth Values indicate lower visual opacity and greater translucency of a material. The reported values are the average of 3 measurements.

Barcol Hardness Test Method

Hardness after cure was measured with a Barcol Hardness meter (model GYZJ-935; Barber Coleman, Inc., Loves Park, Ill.); the meter was monitored for performance consistency using a set of calibration disks provided with the meter. The sample material was packed into a 5-mm diameter spherical cutout in a 2-mm deep Teflon mold. Mylar film was used as a liner on each side of the mold to ensure that the mold was filled completely, and that the sample was flush with the mold surface. The sample was then light cured for 60 seconds, and then allowed to rest under ambient conditions for 5 minutes before testing the hardness per the instrument's instructions.

Adhesion to Dentin (AD) and Enamel (AE) Test Methods

Adhesion to dentin and adhesion to enamel were measured according to the procedure described in U.S. Pat. No. 6,613,812 (Bui et al.), except that a light cure exposure time of 20 seconds was used and 3M ESPE Filtek Z250 composite was used instead of 3M Z100 Restorative.

X-Ray Diffraction (XRD) Test Method

A test sample was mulled in a boron carbide mortar and applied as an ethanol slurry to a zero background specimen holder (aluminum holder with quartz insert). Reflection geometry data were collected in the form of survey scans using a Philips vertical diffractometer, copper Kα radiation, and proportional detector registry of the scattered radiation. The crystallite sizes (D) for the crystalline phases present were calculated from observed peak widths after correction for instrumental broadening as the full width at half maximum using a Pearson VII peak shape model, accounting for α1/α2 separation.

Calcium and Phosphorus Ion Release (CIR) Test Method

Disk-shaped, 1-mm thick by 20-mm diameter samples were cured by exposing them to illumination from a 3M XL3000 dental curing light for 60 seconds on each side of the disk at a distance of 6 mm. The disks were stored in a HEPES-buffered solution at 37° C.; the solution was exchanged periodically, and the ion content measured via inductively coupled plasma spectroscopy (ICP) on a Perkin-Elmer 3300DV Optima ICP unit or via a calcium-selective electrode. The composition of the buffer solution was 1000 g deionized water, 3.38 g NaCl, and 15.61 g HEPES (N-2-hydroxyethylpiperazine-N'-2-ethanesulfonic acid). The ion release rate, microgram (ion)/g(disk)/day, was calculated by dividing the total ion content of the solution (concentration times volume of solution) by the initial disk weight and by the time in days since the last exchange of buffer solution.

Dentin Remineralization Test Method

This method was carried out as described in "Surface Modulation of Dental Hard Tissues" (D. Tantbirojn, Ph.D. thesis, University of Minnesota, 1998), with the following exceptions. Dentin was used instead of enamel; the demineralizing solution was 0.1 ppm $F^-$ from NaF, 1.5 mM $Ca^{+2}$ from $CaCl_2$, 0.9 mM $PO4^{-3}$ from $KH_2PO_4$, 50 mM acetic acid, adjusted to pH=5.0 with 1M KOH; and the mineral content was measured by quantitative image analysis of microradiographs.

Resistance to Demineralization in Dentin Test Method

This method was carried out as described in "Surface Modulation of Dental Hard Tissues" (D. Tantbirojn, Ph.D. thesis, University of Minnesota, 1998), with the following exceptions. Dentin was used instead of enamel; the demineralizing solution was 0.1 ppm $F^-$ from NaF, 1.5 mM $Ca^{+2}$ from $CaCl_2$, 0.9 mM $PO4^{-3}$ from $KH_2PO_4$, 50 mM acetic acid, adjusted to pH=5.0 with 1M KOH; and the extent of acid erosion adjacent to the sample was qualitatively categorized from microradiographs.

Abbreviations, Descriptions, and Sources of Materials

| Abbreviation | Description and Source of Material |
| --- | --- |
| CGP | Calcium glycerophosphate (Avocado Research Chemicals, Lancaster, England) |
| SGP | Sodium glycerophosphate hexahydrate (Sigma Chemical Co., St. Louis, MO) |

-continued

| Abbreviation | Description and Source of Material |
|---|---|
| BisGMA | 2,2-Bis[4-(2-hydroxy-3-methacryloyloxypropoxy)phenyl]propane CAS No. 1565-94-2 |
| TEGDMA | Triethyleneglycol dimethacrylate (Sigma-Aldrich, St. Louis, MO) |
| HEMA | 2-Hydroxyethyl methacrylate (Sigma-Aldrich) |
| PAA/ITA | Copolymer made from a 4:1 mole ratio of acrylic acid:itaconic acid, prepared according to Example 3 of U.S. Pat. No. 5,130,347 (Mitra), MW (average) = 106,000; polydispersity $\rho$ = 4.64. |
| IEM | 2-Isocyanatoethyl methacrylate (Sigma-Aldrich) |
| VBP | Polymer made by reacting PAA/ITA copolymer with sufficient IEM to convert 16 mole percent of the acid groups of the copolymer to pendent methacrylate groups, according to the dry polymer preparation of Example 11 of U.S. Pat. No. 5,130,347. |
| MHP | Methacryloyloxyhexyl phosphate (See Preparation Method described herein) |
| CPQ | Camphorquinone (Sigma-Aldrich) |
| EDMAB | Ethyl 4-(N,N-dimethylamino)benzoate (Sigma-Aldrich) |
| DPIHFP | Diphenyl Iodonium Hexafluorophosphate (Johnson Matthey, Alpha Aesar Division, Ward Hill, NJ) |
| BHT | 2,6-di-tert-butyl-4-methylphenol (Sigma-Aldrich) |
| Filler A | Silane-treated fluoroaluminosilicate glass filler prepared as described for Filler B in U.S. Pat. Publication No. 2003/0198914 (Brennan et al.) |
| Filler B | Silane-treated, nano-sized silica and zirconia particles loosely aggregated as substantially amorphous clusters were prepared in the form of a dry powder filler according to the procedure for "Cluster particles filler" in Column 22 of U.S. Pat. No. 657,572,693 (Wu et al.). |
| Vitrebond Powder | Powder component of VITREBOND Light Cure Glass Ionomer Liner/Base (3M Company, St. Paul, MN) |
| Vitrebond Liquid/Resin | Liquid component of VITREBOND Light Cure Glass Ionomer Liner/Base (3M Company) |
| Vitremer Liquid/Resin | Liquid component of VITREMER Restorative (3M Company) |
| AC-315 | AVALURE Acrylate-Based Copolymer (Noveon, Inc., Cleveland, OH) |

Starting Materials Preparations

6-Methacryloyloxyhexyl Phosphate (MHP)

6-Hydroxyhexyl Methacrylate Synthesis: 1,6-Hexanediol (1000.00 g, 8.46 mol, Sigma-Aldrich) was placed in a 1-liter 3-neck flask equipped with a mechanical stirrer and a narrow tube blowing dry air into the flask. The solid diol was heated to 90° C., at which temperature all the solid melted. With continuous stirring, p-toluenesulfonic acid crystals (18.95 g, 0.11 mol) followed by BHT (2.42 g, 0.011 mol) and methacrylic acid (728.49.02 g, 8.46 mol). Heating at 90° C. with stirring was continued for 5 hours during which time vacuum was applied using tap water aspirator for 5-10 minutes after each half-hour reaction time. The heat was turned off and the reaction mixture was cooled to room temperature. The viscous liquid obtained was washed with 10% aqueous sodium carbonate twice (2×240 ml), followed by washing with water (2×240 ml), and finally with 100 ml of saturated NaCl aqueous solution. The obtained oil was dried using anhydrous $Na_2SO_4$ then isolated by vacuum filtration to give 1067 g (67.70%) of 6-hydroxyhexyl methacrylate, a yellow oil. This desired product was formed along with 15-18% of 1,6-bis(methacryloyloxyhexane). Chemical characterization was by NMR analysis.

6-Methacryloyloxyhexyl Phosphate MHP) Synthesis: A slurry was formed by mixing $P_4O_{10}$ (178.66 g, 0.63 mol) and methylene chloride (500 ml) in a 1-liter flask equipped with a mechanical stirrer under $N_2$ atmosphere. The flask was cooled in an ice bath (0-5° C.) for 15 minutes. With continuous stirring, 6-hydroxyhexyl methacrylate (962.82 g, which contained 3.78 mol of the mono-methacrylate, along with its dimethacrylate by-product as described above) was added to the flask slowly over 2 hours. After complete addition, the mixture was stirred in the ice bath for 1 hour then at room temperature for 2 hours. BHT (500 mg) was added, and then the temperature was raised to reflux (40-41° C.) for 45 minutes. The heat was turned off and the mixture was allowed to cool to room temperature. The solvent was removed under vacuum to afford 1085 g (95.5%) of 6-Methacryloyloxyhexyl Phosphate (MHP) as a yellow oil. Chemical characterization was by NMR analysis.

Strontium Glycerophosphate

A 38.1 wt % solution of $SrCl_2$ (anhydrous) in deionized water (32.0 g) was added to a 34 wt % solution of SGP in deionized water (73.6 g). After thorough mixing, the solution was dried in a glass tray at 90° C. for 8 hours to yield a softly caked powder that was then ground in a mortar and pestle to yield strontium glycerophosphate powder.

Zinc Glycerophosphate

A 59 wt % solution of $ZnCl_2$ (anhydrous) in deionized water (19.5 g) was added to a 34 wt % solution of SGP in deionized water (80.6 g). After thorough mixing, 41.3 g of the resulting solution was mixed with 48.1 g of ethanol to yield a milky white sol that separated in 4 hours into two liquid portions; the thin, clear supernatant was decanted from the thick, syrupy, slightly turbid portion on the bottom. This bottom portion was dried at 90° C. for 8 hours to yield zinc glycerophosphate as thin, friable flakes.

Silver Glycerophosphate

A 27 wt % solution of $AgNO_3$ in deionized water (24.1 g) was added to a 34 wt % solution of SGP in deionized water (56.3 g) and mixed thoroughly. After sitting for 4 hours, the supernatant was decanted to recover a powdery precipitate, which was dried in air for 3 days, and then ground in a mortar and pestle to yield silver glycerophosphate powder.

Zirconium Glycerophosphate

Zirconyl acetate (19.7 g; Magnesium Elektron, Inc., Flemington, N.J.) was added to a 34 wt % solution of SGP in deionized water (66.3 g) and mixed thoroughly. The resulting solution was dried at 90° C. for 4 hours, and then further at 50° C. for 8 hours to yield thin, friable flakes that were then ground in a mortar and pestle to yield zirconium glycerophosphate powder.

Resins A, B, C and D

Resins A, B, C and D were prepared by combining the ingredients as shown in Table 1.

TABLE 1

Compositions of Resins A, B, C, and D

| Ingredient (Weight %) | Resin A | Resin B | Resin C | Resin D |
|---|---|---|---|---|
| VBP | 43.43 | 43.00 | 0 | 0 |
| HEMA | 22.27 | 22.05 | 17.00 | 0 |
| BisEMA6 | 0 | 0 | 0 | 32.00 |
| BisGMA | 0 | 0 | 27 | 0 |
| TEGDMA | 0 | 0 | 38 | 32.00 |
| MHP | 0 | 0 | 14.34 | 0 |
| PM-2 | 0 | 0 | 0 | 33.15 |
| Water | 34.04 | 33.70 | 0 | 0 |
| CPQ | 0.30 | 0.30 | 0.32 | 0.3 |
| DPIHFP | 0 | 1.00 | 0.53 | 0 |
| BHT | 0.05 | 0.05 | 0.39 | 0.15 |
| EDMAB | 0 | 0 | 2.42 | 2.4 |
| TOTAL: | 100 | 100 | 100 | 100 |

Examples 1A-J

CGP Aqueous Compositions

CGP powder was dissolved in Vitremer Resin at concentrations of 2% by weight and 10% by weight to form clear, homogeneous resin compositions (Examples 1A and 1B, respectively). Both compositions were clear, homogeneous, and free of precipitates and gelation at over 8 months under ambient conditions. A cured disk of Example 1B was subjected to Powder X-Ray Diffraction (XRD) according to the Test Method described herein and showed no crystalline phases and a broad peak at d~5.0 Å characteristic of amorphous materials. The powder XRD pattern for the as-received CGP showed CGP as the main crystalline phase present with an apparent crystallite size of 140 Å, and trace (~5%) amounts of an unidentified phase.

CGP powder was dissolved in Resin B at concentrations of 4% by weight and 10% by weight to form clear, homogeneous resin compositions (Examples 1C and 1D, respectively). The refractive index of Example 1D (measured on an Abbe Refractometer) was 1.4560 as compared to 1.449 for Resin B.

CGP powder was dissolved in Resin B at a concentration of 25% by weight to form a clear, homogeneous resin composition (Example 1E). The composition was observed to be much more viscous than Resin B.

CGP powder was compounded with Vitremer Resin and with Resin C each at a concentration of 55% by weight to form viscous paste compositions (Examples 1F and 1G, respectively). The spectral opacity values (measured according to the Test Method described herein) of Examples 1F and 1G were determined to be 16.6 and 76.0, respectively.

A resin (18.3 g) of CGP (4% by weight) in Resin B was blended with a resin (7.2 g) of $Na_2FPO_3$ (Alfa Aesar, Ward Hill, Mass.) (10% by weight) in Vitremer Resin to form a clear, homogeneous resin composition containing 2.9% CGP and 2.8% $Na_2FPO_3$ (Example 1H). The composition was observed to remain clear, homogeneous, and fluid for greater than 6 months at ambient conditions.

CGP (10% by weight) and $NaPF_6$ (Alfa Aesar) (3% by weight) were blended into Resin B to form a clear, homogeneous resin composition (Example 1I).

CGP (8% by weight) was blended into a solution of $Na_2FPO_3$ (12%) in deionized water to form a white, stable dispersion (Example 1J) with a few large particles that settled.

Examples 1H-1J demonstrate that stable, aqueous compositions containing CGP can be prepared with high levels of co-dissolved calcium and fluoride.

Examples 2-4 and Comparative Examples 1-2

RMGI Compositions Containing CGP

Liquid resin compositions containing CGP (Examples 1A, 1C, and 1D) were spatulated with Vitrebond Powder at a Powder/Liquid (P/L) ratio of 1.2/1 to afford homogeneous RMGI pastes designated Examples 2-4, respectively. These pastes were evaluated for compressive strength (CS), diametral tensile strength (DTS), work time, spectral opacity (SO), and adhesion to dentin (AD) and enamel (AE) according to the Test Methods described herein and the results compared to those from the commercial VITREBOND Light Cure Glass Ionomer Liner/Base product (Comparative Examples (CE) 1 and 2). (For the AD and AE tests of these materials, an additional step was added: a dental adhesive (3M ESPE Singlebond Plus dental adhesive) was brushed over the cured material and then light-cured for 10 sec before application of the composite.) The data are provided in Table 2 and show that the physical properties of the CGP-containing RMGI compositions were generally the same as for the commercial VITREBOND product.

TABLE 2

| Ex. | Powder | Liquid | P/L | SO | CS MPa (SD) | DTS MPa (SD) | Work Time Min:Sec | Dentin Adh. MPa (SD) | Enamel Adh. MPa (SD) |
|---|---|---|---|---|---|---|---|---|---|
| 2 | Vitrebond | Ex. 1A (2% CGP) | 1.2/1 | 73.77 | NT* | NT | NT | NT | NT |
| 3 | Vitrebond | Ex. 1C (4% CGP) | 1.2/1 | 75.89 | 114 (12.14) | 22.22 (4.17) | 4:52 | 6.50 (2.08) | 16.58 (0.57) |
| 4 | Vitrebond | Ex. 1D (10% CGP) | 1.2/1 | NT | 128 (11.80) | 21.87 (3.13) | NT | 5.65 (0.96) | 8.29 (2.40) |

TABLE 2-continued

| Ex. | Powder | Liquid | P/L | SO | CS MPa (SD) | DTS MPa (SD) | Work Time Min:Sec | Dentin Adh. MPa (SD) | Enamel Adh. MPa (SD) |
|---|---|---|---|---|---|---|---|---|---|
| CE 1 | Vitrebond | Vitrebond | 1.4/1 | 77.19 | 113 (9.50) | 25.32 (1.73) | 4:55 | 6.86 (5.59) | 12.94 (1.03) |
| CE 2 | Vitrebond | Vitrebond | 1.2/1 | NT | 108 (6.55) | 21.60 (0.89) | NT | NT | NT |

*NT—Not Tested

Examples 5 and 6

Acidic Resin Compositions Containing CGP

Resin compositions containing CGP (Examples 5 and 6) were prepared by combining the ingredients shown in Table 3. The resulting pastes were evaluated for compressive strength, diametral tensile strength, spectral opacity, and adhesion to dentin (AD) and enamel (AE) according to the Test Methods described herein and the results are provided in Table 3. (For the AD and AE tests of these materials, a thin layer of the material was allowed to sit for 30 sec before light-curing for 30 sec.) Both Examples 5 and 6 showed excellent strength and adhesion to tooth structure.

TABLE 3

| Example | Composition (Numbers are Weight %) | Spectral Opacity | CS MPa (SD) | DTS MPa (SD) | Dentin Adhesion MPa (SD) | Enamel Adhesion MPa (SD) |
|---|---|---|---|---|---|---|
| 5 | CGP - 25<br>MHP - 60<br>Filler A - 15 | 79.26 | 197 (90.39) | 22.15 (3.12) | 10.86 (2.29) | 12.75 (3.70) |
| 6 | CGP - 10<br>MHP - 45<br>Filler A - 10<br>Filler B - 35 | 58.99 | 198 (34.09) | 35.74 (2.56) | 9.77 (2.58) | 13.36 (3.70) |

Example 7 and Comparative Example 3

Self-Adhesive Composition Containing CGP

CGP (5% by weight) was added to the powder component of RelyX Unicem Cement in a MAXICAP capsule (3M Company) and then mixed in a ROTOMIX mixer for 10 seconds to afford a paste that was designated Example 7. Example 7 was evaluated for compressive and diametral tensile strengths according to the Test Methods described herein and the results compared to those for the commercial RelyX Unicem Maxicap Self-Adhesive Universal Resin Cement product (Comparative Example (CE) 3). The data are provided in Table 4 and show that the physical properties of the CGP-containing cement composition were basically the same as for the commercial RelyX Unicem cement.

TABLE 4

| Example | Composition | Compressive Strength MPa | Diametral Tensile Strength MPa |
|---|---|---|---|
| 7 | RelyX Unicem + CGP | 201 ± 13 | 41 ± 4 |
| CE 3 | RelyX Unicem | 199 ± 20 | 51.82 ± 14 |

Example 8 and Comparative Example 4

Adhesive Composition Containing CGP

Example 1D (Resin B+10% CGP) was used as the Liquid B component in ADPER PROMPT L-POP Self-Etch Adhesive product (3M Company) and evaluated for shear adhesion to enamel according to the Test Method described herein and the results compared to those for the commercial ADPER Adhesive product (Comparative Example (CE) 4). (For the AE test of these materials, liquids A and B were mixed in a well and the resulting adhesive was brushed on the tooth surface for 20 sec, gently air-dried for 10 sec, and then light-cured for 10 sec.) The data are provided in Table 5.

TABLE 5

| | Composition | | Droplets | Enamel Adhesion |
|---|---|---|---|---|
| Example | Liquid A | Liquid B | A:B | MPa (SD) |
| 8 | ADPER Product | Example 1D | 1:1 | 7.43 (1.47) |
| CE 4 | ADPER Product | ADPER Product | 1:1 | 11.89 (2.26) |

Examples 9A and 9B

Hardenable Resin Containing Zinc Glycerophosphate

Zinc nitrate hexahydrate (0.27 g) was dissolved in Resin B (9.2 g) to yield a clear solution; then, SGP (0.26 g) was added, and dissolved to form a clear liquid (designated Example 9A) containing zinc glycerophosphate (formed in situ). Example 9A (after spatulation with Vitrebond powder at a powder/liquid ratio of 1:1) had a Barcol Hardness of 52.7.

Zinc glycerophosphate (see Starting Materials Preparations) was added to Resin B at a level of 3 wt % to form a clear liquid that was designated Example 9B. Example 9B (after spatulation with Vitrebond powder at a powder/liquid ratio of 1:1) had a Barcol Hardness of 52.7. Resin B (a clear liquid; after spatulation with Vitrebond powder at a powder/liquid ratio of 1:1) had a Barcol Hardness of 31.7.

Examples 10A and 10 B

Hardenable Resin Containing Strontium Glycerophosphate

Filler A (41%), Resin D (40%) and strontium glycerophosphate (19%; see Starting Materials Preparations) were mixed to form a thin, flowable paste that was designated Example 10A. A light-cured 1-mm thick disk of Example 10A had a Visual Opacity measured on a Macbeth Densitometer of 0.243.

Strontium glycerophosphate (see Starting Materials Preparations) was added to Resin B at a level of 3 wt % to form a clear liquid that was designated Example 10B. Example 10B (after spatulation with Vitrebond powder at a powder/liquid ratio of 1:1) had a Barcol Hardness of 46.7.

Example 11

Hardenable Resin Containing Silver Glycerophosphate

Filler A (65%), Resin D (32%) and silver glycerophosphate (3%; see Starting Materials Preparations) were mixed to form a thin, flowable paste that was designated Example 11. A light-cured 1-mm thick disk of Example 11 had a Visual Opacity measured on a Macbeth Densitometer of 0.546.

Examples 12A and 12B

Hardenable Resin Containing Zirconium Glycerophosphate

Filler A (65%), Resin D (32%) and zirconium glycerophosphate (3%; see Starting Materials Preparations) were mixed to form a thin, flowable paste that was designated Example 12A. A light-cured 1-mm thick disk of Example 12A had a Visual Opacity measured on a Macbeth Densitometer of 0.380.

Zirconium glycerophosphate (see Starting Materials Preparations) was added to Vitrebond powder at a level of 3 wt % to form a new powder that could be useful as a dental filler. The new powder (after spatulation with Resin B at a powder/liquid ratio of 1:1 to form a paste designated as Example 12B) had a Barcol Hardness of 20. Vitrebond powder (after spatulation with Resin B at a powder/liquid ratio of 1:1) had a Barcol Hardness of 31.7.

Examples 13-16

Tooth Coating Compositions Containing CGP

CGP (8.6% by weight) was blended with 13.3% of a solution of sodium monofluorophosphate ($Na_2FPO_3$; 12% in deionized water) and with 78.1% of a solution of 45% PAA/ITA copolymer, 45% ethanol, and 10% Nalco 1042 colloidal silica to form a homogeneous, milky white colloid that was designated Example 13. The material remained homogeneous and flowable at two weeks at ambient conditions, and formed a translucent coating after applying to a glass slide and drying.

CGP (11% by weight) was blended with 89% of a solution of 30% AVALURE AC-315 polymer in ethanol to form a cloudy dispersion that was designated Example 14. Sediment settled from the dispersion after 1-2 days, but readily redispersed upon mixing. The dispersion formed a hard, cloudy coating after applying to a glass slide and drying.

CGP (9% by weight) was blended with 21% of a solution of $Na_2FPO_3$ (12% in deionized water) and with 70% of a solution of 45% PAA/ITA copolymer in ethanol to form a turbid sol (Example 15) that exhibited sedimentation after several hours.

CGP (12% by weight) was blended with 15% of a solution of $Na_2FPO_3$ (12% in deionized water) and with 73% of a solution of 45% PAA/ITA copolymer, 45% ethanol, and 10% Nalco 1042 colloidal silica to form a homogeneous, turbid, stable sol that was designated Example 16.

Calcium and Phosphorus Ion Release Evaluations

Example 1F (55% CGP in Vitremer Resin), Example 1G (55% CGP in Resin C), Example 2 (2% CGP in RMGI composition), and Example 3 (4% CGP in RMGI composition) were evaluated for calcium and phosphorus release over time according to the Test Method described herein. Results are reported for the ICP method (calcium and phosphorus ions via inductively coupled plasma spectroscopy) and for the calcium-selective electrode (Ca-E) method (calcium ions only) and are provided in Table 6. These results show that all four Examples exhibited sustained release of calcium ion through 60 days and three of the Examples (1F, 1G, and 2) exhibited sustained release through 180 days.

TABLE 6

Release of Calcium and Phosphorus Ions over Time

| | Day 7 | | | Day 30 | | | Day 60 | | | Day 180 | | |
|---|---|---|---|---|---|---|---|---|---|---|---|---|
| | ICP | | Ca-E | ICP | | Ca-E | ICP | | Ca-E | ICP | | Ca-E |
| Ex. | Ca | P | Ca | Ca | P | Ca | Ca | P | Ca | Ca | P | Ca |
| 1F | 6126 | 8841 | NT | 387.5 | 102.3 | NT | 143.1 | 5.07 | NT | NT | NT | 33.87 |
| 1G | NT | NT | 1007 | NT | NT | 384.9 | NT | NT | 28.66 | NT | NT | NT |
| 2 | NT | NT | NT | 8.77 | 215.4 | NT | NT | NT | 4.74 | NT | NT | NT |
| 3 | NT | NT | 4.70 | NT | NT | 12.29 | NT | NT | 11.37 | NT | NT | NT |

All Values in Units of Microgram (Ion)/g (Disk)/day

Dentin Remineralization Evaluations

Example 4 (10% CGP in RMGI composition) was evaluated for dentin remineralization according to the Test Method described herein and showed remineralization after 3 weeks adjacent to the applied cement in the area of the exposed lesion.

Resistance to Demineralization in Dentin Evaluations

Example 4 (10% CGP in RMGI composition) and comparative Examples 1 and 5 (VITREBOND Light Cure Glass Ionomer Liner/Base and FILTEK Z250 Universal Restorative System, respectively) were evaluated for resistance to demineralization in dentin according to the Test Method described herein. The resulting microradiographs and associated data (Table 7) showed that the VITREBOND product enhanced resistance to acid attack versus FILTEK Z250 and that Example 4 enhanced this resistance dramatically.

TABLE 7

Percent of Samples in Each Lesion Category

| Lesion Category | VITREBOND | Z250 | Ex. 6 |
|---|---|---|---|
| Full Lesion | 27.3 | 100.0 | 0.0 |
| Lesion thinner near material | 33.3 | 0.0 | 60.9 |
| Intact dentin near material, lesion farther away | 39.4 | 0.0 | 30.4 |
| No lesion discernible | 0.0 | 0.0 | 8.7 |

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A dental composition comprising:
a hardenable resin comprising water, wherein the hardenable resin is polymerizable and/or crosslinkable; and
a phosphate salt of the formula:

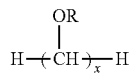

where x=2-4;
each R is independently H or $P(O)(O^-)_2(M^{+n})_{2/n}$, with the proviso that at least one R group is $P(O)(O^-)_2(M^{+2n})_{2/n}$ and at least one R group is H; and
M is a metal of valence n,
wherein the phosphate salt is dissolved in the hardenable resin of the dental composition.

2. The dental composition of claim 1, where x=3.

3. The dental composition of claim 1, wherein M is selected from the group consisting of Group 2 metals, Group 3 metals, transition metals, Lanthanides, and combinations thereof.

4. The dental composition of claim 3, wherein M is selected from the group consisting of Mg, Ca, Sr, Ba, Zn, Ag, Zr, Sn, and combinations thereof.

5. The dental composition of claim 4, wherein M is Ca.

6. The dental composition of claim 1, wherein the hardenable resin comprises acid functionality.

7. The dental composition of claim 6, wherein the acid functionality comprises carboxylic acid functionality, phosphoric acid functionality, phosphonic acid functionality, sulfonic acid functionality, or combinations thereof.

8. The dental composition of claim 1, further comprising an initiator system.

9. The dental composition of claim 1, further comprising an additional filler.

10. The dental composition of claim 1, wherein the hardenable resin comprises an ethylenically unsaturated compound.

11. The dental composition of claim 10, wherein the ethylenically unsaturated compound is selected from the group consisting of an ethylenically unsaturated compound with acid functionality, an ethylenically unsaturated compound without acid functionality, and combinations thereof.

12. The dental composition of claim 1, wherein the composition is selected from the group consisting of dental primers, dental adhesives, cavity liners, cavity cleansing agents, cements, coatings, varnishes, orthodontic adhesives, restoratives, sealants, desensitizers, and combinations thereof.

13. The dental composition of claim 1, further containing a solvent, wherein the solvent is selected from the group consisting of propanol, ethanol, acetone, methyl ethyl ketone, ethyl acetate, dimethylformamide, dimethylacetamide, dimethylsulfoxide, 1-methyl-2-pyrrolidinone, and a combination thereof.

14. The dental composition of claim 1, wherein the phosphate salt is selected from the group consisting of calcium glycerophosphate, zinc glycerophosphate, magnesium glycerophosphate, strontium glycerophosphate, tin glycerophosphate, zirconium glycerophosphate, and silver glycerophosphate.

15. The dental composition of claim 1, wherein the phosphate salt is calcium glycerophosphate.

16. The dental composition of claim 1, wherein the composition comprises calcium glycerophosphate, an ethylenically unsaturated compound without acid functionality, and an ethylenically unsaturated compound with acid functionality.

17. The dental composition of claim 16, wherein the ethylenically unsaturated compound without acid functionality is a hydroxy functional methacrylic acid ester.

* * * * *

UNITED STATES PATENT AND TRADEMARK OFFICE
CERTIFICATE OF CORRECTION

PATENT NO. : 10,137,061 B2
APPLICATION NO. : 11/719469
DATED : November 27, 2018
INVENTOR(S) : Richard Rusin et al.

Page 1 of 1

It is certified that error appears in the above-identified patent and that said Letters Patent is hereby corrected as shown below:

In the Specification

Column 1
Line 67, delete "$(M^{+n})_{2/1}$," and insert -- $(M^{+n})_{2/n}$, --, therefor.

Column 4
Line 31, delete "unimodial" and insert -- unimodal --, therefor.
Line 31, delete "polymodial" and insert -- polymodal --, therefor.

Column 13
Line 4, delete "quarternary" and insert -- quaternary --, therefor.

Column 19
Line 61, delete "MHP)" and insert -- (MHP) --, therefor.

Column 25
Line 1, delete "10 B" and insert -- 10B --, therefor.

Signed and Sealed this
Tenth Day of September, 2019

Andrei Iancu
*Director of the United States Patent and Trademark Office*